United States Patent
Grossmann et al.

(10) Patent No.: US 10,151,688 B2
(45) Date of Patent: Dec. 11, 2018

(54) METHODOLOGY FOR THE IDENTIFICATION OF MATERIALS THROUGH METHODS OF COMPARISON OF THE SPECTRUM OF A SAMPLE AGAINST A REFERENCE LIBRARY OF SPECTRA OF MATERIALS

(71) Applicants: Optionline LLC, Garden City, NY (US); Optionline Editora Eireli, Sao Paulo (BR)

(72) Inventors: Luiz Grossmann, Sao Paulo (BR); Marco Antonio Borges, Sao Paulo (BR)

(73) Assignees: Optionline LLC, Garden City, NY (US); Optionline Editora Eireli, Sao Paulo-SP (BR)

( * ) Notice: Subject to any disclaimer, the term of this patent is extended or adjusted under 35 U.S.C. 154(b) by 0 days.

(21) Appl. No.: 15/495,173

(22) Filed: Apr. 24, 2017

(65) Prior Publication Data

US 2018/0059011 A1    Mar. 1, 2018

(30) Foreign Application Priority Data

Aug. 26, 2016   (BR) .............................. 102016019770

(51) Int. Cl.
*G01N 21/31*    (2006.01)
*G01N 21/359*   (2014.01)
*G01N 21/27*    (2006.01)

(52) U.S. Cl.
CPC ......... *G01N 21/314* (2013.01); *G01N 21/278* (2013.01); *G01N 21/359* (2013.01); *G01N 2021/3196* (2013.01); *G01N 2201/0221* (2013.01); *G01N 2201/12746* (2013.01)

(58) Field of Classification Search
CPC ............... G01N 21/314; G01N 21/359; G01N 2201/12746
See application file for complete search history.

(56) References Cited

U.S. PATENT DOCUMENTS

| | | | |
|---|---|---|---|
| 5,308,982 A * | 5/1994 | Ivaldi | G01J 3/433 250/339.12 |
| 2006/0249680 A1 | 11/2006 | Hu et al. | |
| 2010/0158385 A1 * | 6/2010 | Jeung | G01N 23/087 382/191 |
| 2014/0231626 A1 | 8/2014 | Nelson et al. | |

FOREIGN PATENT DOCUMENTS

| | | |
|---|---|---|
| BR | PI 0205413-2 A | 7/2004 |
| BR | PI 0504496-0 A | 6/2007 |
| EP | 563998 B1 | 11/1998 |
| GB | 2321104 A | 7/1998 |

* cited by examiner

*Primary Examiner* — Mark R Gaworecki
(74) *Attorney, Agent, or Firm* — Alston & Bird LLP

(57) ABSTRACT

A method of comparison of spectra from the spectrum of a sample and at least one spectrum of a reference library is provided. The method involves: obtaining at least one relevant spectral peak from the sample spectrum and comparing each of the relevant spectral peaks obtained with the spectra in the reference library. Methods are also described for: comparison of spectra from the second derivative of the sample spectrum and the second derivative of the reference library spectra; and comparison of spectra with the previous identification of the major component of a sample, which involves correlating triangularly the spectra of the sample, the reference and the major component.

14 Claims, 13 Drawing Sheets

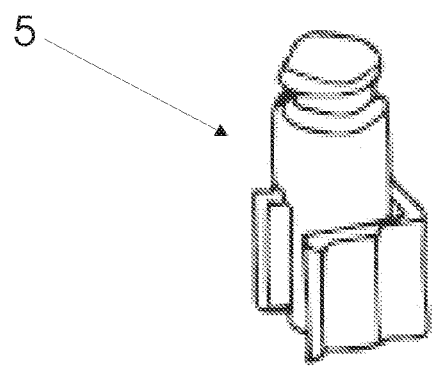
FIG. 13 (a)
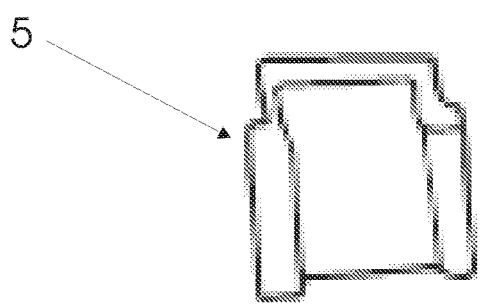
FIG. 13 (b)
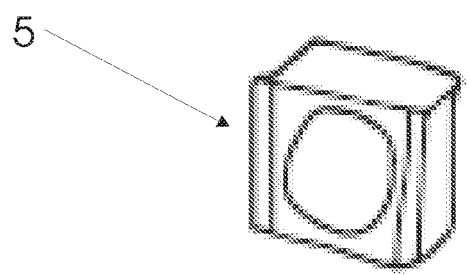
FIG. 13 (c)
FIG. 13

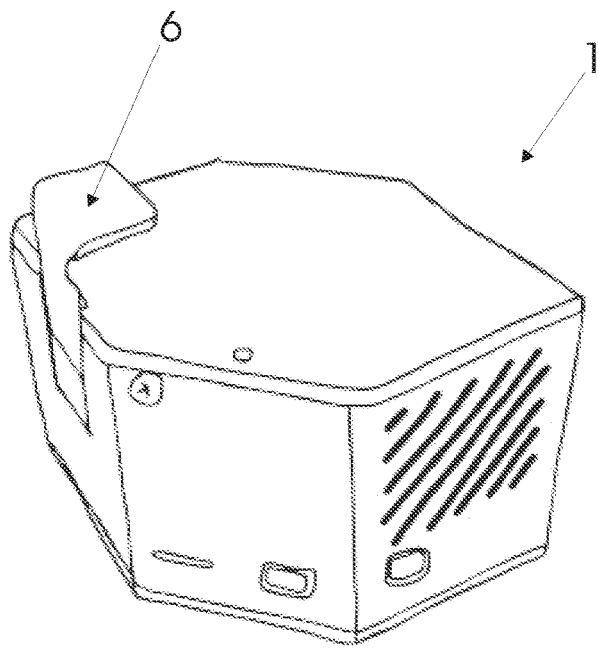
FIG. 14 (a)
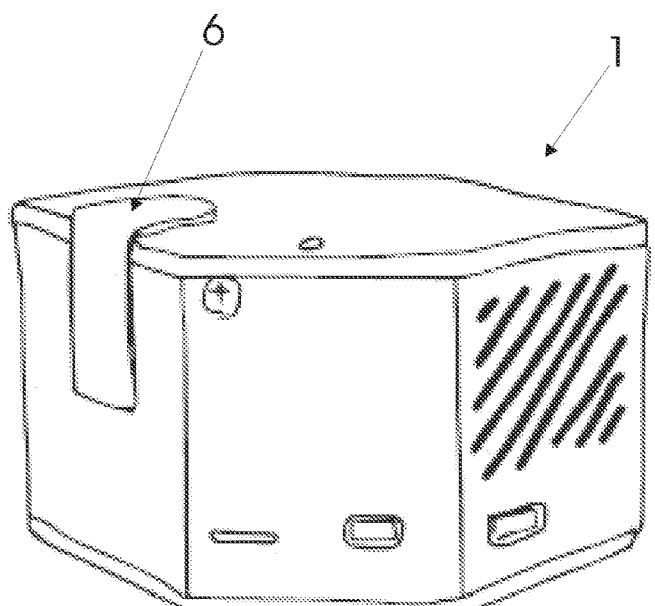
FIG. 14 (b)
FIG. 14

METHODOLOGY FOR THE IDENTIFICATION OF MATERIALS THROUGH METHODS OF COMPARISON OF THE SPECTRUM OF A SAMPLE AGAINST A REFERENCE LIBRARY OF SPECTRA OF MATERIALS

CROSS-REFERENCE TO RELATED APPLICATION

This application claims priority to and full benefit of Brazilian Patent Application No. BR102016019770-8, filed on Aug. 26, 2016, the contents of which as are hereby incorporated by reference herein in their entirety.

BACKGROUND

Related Field

The present invention relates to a methodology for the identification of materials through the comparison of spectra produced in the near infrared range (NIR—near infrared spectroscopy) involving several steps described below as methods.

The technique begins with the method that takes as a basis the main peaks of the sample spectrum and of the reference, entitled "Method of Main Peaks", which produces very satisfactory results with a minimum computational processing time.

A second step involves the technique to compare the sample spectrum and the reference in finer regions of this spectrum through the second derivative of the spectrum, especially in cases where the main peaks are not apparent or representative, or where a further development is necessary to increment the first step, in the method entitled "Method of Variance".

The present invention also relates to a third stage that involves a method for identifying a non-major component in a sample, through the comparison of spectra accomplished with the neutralization of the effect of a major component previously identified in the sample, in the method entitled "Method of Triangulation".

Present invention also describes mounting brackets to standardize the readings made in different devices, which ensure the correct positioning of the samples, specific holders for positioning pharmaceutical samples, and a calibration device to standardize the readings. In this way, it is possible to promote the compatibility between different devices and libraries in a portable device for the evaluation of a sample spectrum in accordance with the methodology proposed in the present invention, and effectively produce satisfactory results in the identification of unknown materials in the samples.

Description of Related Art

An exemplary and desirable embodiment of the present invention is the analysis of pharmaceuticals, since the falsification and sale of low quality medicines have become endemic in modern society.

The high price of products, the difficulty of access by the poorest people, the difficulty of inspection among other reasons, often cause pharmaceuticals to be marketed without the active ingredient or with inadequate and even prohibited active ingredients, as seen in unauthorized inclusions of compounds for a desired functional property.

Several analytical methods are commonly recommended by the pharmacopoeias for the identification of drugs (active ingredients), such as thin layer chromatography, gas chromatography, infrared, ultraviolet, colorimetric reactions, etc. However, almost all existing methods are expensive, time-consuming and usually require prior sample preparation, acquisition of high cost standards with limited expiration periods and the need for a conventional analytical support laboratory for conducting the tests. Additionally, virtually all methods require the destruction of the samples to be analyzed.

Because of these difficulties, the search for counterfeit and off standard goods by the authorities usually involves solely checking the packaging, tracking the supply chain and the analysis of the documentation that could lead to suspicions of tampering or falsification and thus, withholding suspicious samples for further analysis.

It is not likely that in such cases a sample is retained due to its composition, but rather due to evidence other than its chemistry. Thus, the present invention aims, amongst other aspects, to overcome this gap.

The prior art reveals chemometric techniques and NIR spectrometry (Near Infrared Spectroscopy) for the analysis of chemical composition and quality control of medicines. NIR corresponds to the electromagnetic spectrum range in the 800-2500 nm (nanometers) region. In this range, the absorbances correspond to "overtones" and combinations of secondary molecular vibrations, whose fundamental vibrations occur in the mid-infrared range of the electromagnetic spectrum.

The absorbances produced tend to be weaker in the NIR than those in the corresponding mid-infrared range. In the case of NIR, samples can be analyzed without prior preparation or dilution, but produce spectra that are significantly more complex to analyze when compared to mid-infrared, containing many overlapping peaks, and more amounts of data, as well as noise.

The strength of NIR is the ease in the use of samples without prior preparation and glass bottles as containers, since many materials, such as borosilicate, for example, are transparent to NIR radiation, and don't interfere with the readings.

The intensity of the radiation reflected by the sample is measured in each wavelength and compared with the intensity of the radiation reflected at the same wavelength of a reference material such as, for example, a ceramic disc or spectralon which has a high rate of diffuse reflection. Spectra are dependent on the chosen reference and the reproducibility thereof can be a problem when it is necessary to perform the transfer of the spectrum from one device to another.

The ability of NIR spectroscopy to detect both physical and chemical aspects implies that the method can be used to recognize authentic standards and falsifications, and methods such as PCA (Principal Component Analysis) or Maximum Wavelength Distance are usually employed for this purpose.

The instrumentation routinely used for NIR measurements is similar to that employed in UV spectrometry or visible light, based on fixed wavelength readings, scanning or diode array systems. The instruments make use of Tungsten/Halogen bulbs that serve as a source of energy. Lead sulfide, silicon and/or indium gallium arsenide (InGaAs) detectors are used. The instruments contain controllers and/or microprocessors that allow for reading in seconds.

The prior art discloses documents that cover the use of the NIR technique to analyze medicines and chemical products, such as PI 0205413-2.

This document describes a method for the quantification of additives in hydrocarbons through near infrared spectroscopy, which uses results of mathematical treatments and multivariate regression models applied to numeric data extracted from the spectra adsorption acquired from hydrocarbon samples with and without additives, in the wavelength range in the near infrared (NIR) area. The method, based on multivariate analysis, takes into account the influence of all variables, that is, the spectrum as a whole.

Additionally, PI 0504496-0 describes a method for direct determination of acetaminophen in powdered pharmaceutical samples by fluorescence spectroscopy related to the demonstration of the fluorescence of acetaminophen (API) in solid state and to the development and optimization of a methodology for determining this compound in solid matrix through fluorescence spectroscopy, without pretreatment of the sample.

To this end, optical fiber is employed as a radiation conductor and measurements are performed directly on the pulverized sample containing the active substance (API) diluted in lactose, starch, talc, polyvinylpyrrolidone and stearic acid. In this method, sample preparation and creation of a statistical model prior to the analysis (calibration) are required.

In this regard, document EP 0.563.998 presents a method for detecting bio-molecules, toxic substances, polymers and drugs using fluorescence spectroscopy through marker dyes and life cycle times. Accordingly, it is emphasized that the present invention does not use any kind of markers to identify the sample.

Additionally, document GB 2.321.104 suggests a method for detecting a single substance in a library of compounds, using support substances, known as receptors, that can bind chemically to the desired substance forming a complex. A molecular weight-based analysis is performed to identify the complex formed. In contrast, the present invention does not depend on other supporting substances or molecular weight analysis.

Patent application US2006/249680 is directed to an instrument and method for identifying a drug through NIR. The method employs known techniques for dimensionality reduction, described as Principal Component Analysis (PCA) and unsupervised pattern recognition techniques such as clustering.

Several readings are made (nominally between 4 and 5 samples are suggested) for various types of drugs, called reference drugs, and an unknown drug is compared to the others, using the Euclidean distance between the known spectra and the spectrum of the unknown drug sample.

The shortest approximation between the pairs of spectra shows which would be the most likely drug. In this method, there is an inherent limitation to the number of drugs against which to compare the unknown sample, which could hardly exceed ten. The process also involves large consumption of computational effort and time, ultimately an obstacle to its use.

Additionally, US 2014/0231626 presents a specific target material detection system in a sample subjected to a visible light beam and NIR, through a detector and a hyperspectral imaging of the sample, comparing it to previous hyperspectral imaging of samples that had previously identified target material. The present invention differs from the abovementioned method in that it does not require a prior sample training or knowledge of the sample with a given target material content. Additionally, the processing takes place with the aid of a tunable filter to generate the various desired wavelengths, which also differs from the subject matter disclosed in the present invention.

The methodology and the proposed device in the present invention, as is better explained below, are based on NIR (near infrared spectroscopy) and allow a quick check of the identity of a sample using a low-cost portable device, without the necessary preparation or destruction of the sample, and the possibility of real-time online comparison with existing libraries of reference substance spectra (reference library).

BRIEF SUMMARY

The present invention aims to identify the major component in a sample of material responsive to the electromagnetic stimulus in the Near Infrared (NIR) wavelength range through the provision of a method of comparison of spectra from the identification and comparison of at least one relevant spectral peak in the sample against a spectra reference library.

It is also the objective of the present invention to provide the identification of a major component in a sample of material responsive to energy stimulus in the NIR range through the provision of a method of spectral matching by the comparison of the second derivative of a spectrum against a reference library, usually when the identification of the main peaks in the sample is not possible or when an increase in the accuracy of the identification is desired.

An additional embodiment of the present invention is the provision of a method to identify a non-major component in a sample, after the prior identification of a major component present in the sample, whose effect in the sample spectrum one wishes to neutralize. The comparison between the spectra in the sample and the reference library is performed using a triangular relationship between the sample spectrum, the reference spectra and the spectrum of the major component.

The present invention also aims at providing a method of comparison between spectra with prior identification of the major component in a sample that comprises the step of subtracting the value of the correlation between sample and reference from the value of the correlation between reference and the major component.

An additional embodiment of the present invention is the provision of a method of comparison between the spectra with the identification of the major component from the analysis of the second derivative of the reference spectrum.

The present invention also aims at providing standardization mechanisms combined with a portable device to evaluate the spectrum of a sample and said device is able to perform the methodology proposed in the present invention.

An additional embodiment of the present invention is the provision of a portable device for the evaluation of a sample spectrum, in which said sample is always located at the same distance and position in relation to the spectral reading element in all the evaluations performed by the device.

An additional embodiment of the present invention is the provision of a calibration device which can be combined with a portable device for the evaluation of a sample spectrum, and the calibration device configured to secure the same standard in all the evaluations performed by the portable device in equivalent samples.

An additional embodiment of the present invention is the application of the proposed methodology for identifying a test sample.

The present invention provides a quick method for comparing the spectrum of a sample against at least one spectrum of a Pref1, Pref2, Pref3 reference library. This method comprises the following steps: obtaining at least one relevant spectral peak P1, P2, P3 and P4 from the sample spectrum, and comparing each of the relevant spectral peaks P1, P2, P3 and P4 with the spectra of the reference library Pref1, Pref2, Pref3.

It provides a quick method for comparing the spectrum of a sample and at least one spectrum of a Pref1, Pref2, Pref3 reference library, and the method comprises the following steps: obtaining a second derivative from both the sample spectrum and the reference library spectrum and correlating them.

The objectives of the present invention are further achieved through a method of comparison between the spectra with the identification of the major component of a sample, and the method comprises the following steps: obtaining a spectrum of a sample and of a reference, given the prior identification of a major component in the sample, correlating the sample spectrum with the reference spectrum, and correlating the reference spectrum with the spectrum of the major component.

Additionally, fastening and positioning devices for the samples, and a calibration device are proposed to be used in a portable device for evaluating the spectrum of a sample. The calibration device can be combined with a measuring window for the portable device, using the fastenings arranged in the measuring window, wherein the calibration device is configured as a metal plate treated with a titanium dioxide-based pigment paint and, additionally, the calibration device is configured to establish a complete seal of the measuring window. The fastening and positioning devices of the samples must also be treated with the titanium dioxide-based pigment paint.

We also propose a portable device to evaluate a sample spectrum, which comprises a spectral reading element associated with a housing for the portable device, wherein the spectral reading element is directed to a measuring window in the portable device, the measuring window comprising fasteners configured to position the sample through specific holders at a fixed distance from the spectral reading element in all evaluations performed by the portable device.

BRIEF DESCRIPTION OF THE FIGURES

The present invention will be, hereinafter, described in more detail based on an execution example represented in the drawings. The figures show:

FIG. 13—is an exemplary representation of sample fasteners used in the portable device proposed in the present invention, wherein FIG. 13 (a) is a storage carrier for liquid or powder sample and FIGS. 13 (b) and 13 (c) show carriers for solid samples;

FIG. 14—is an exemplary representation of the portable device for evaluation of a sample spectrum, wherein said device comprises a calibration device, while FIG. 14 (a) shows the calibration device being positioned in the portable device, and FIG. 14 (b) shows the calibration device already positioned in the portable device.

DETAILED DESCRIPTION OF VARIOUS EMBODIMENTS

The present invention relates to the identification of a material responsive to an electromagnetic stimulus in the NIR range, initially a method of comparison of spectra from the sample spectrum and at least one reference library spectrum.

As a reference library, it is understood to be a database that gathers a certain number of spectra of known pure materials.

The method of comparison between spectra initially proposed in the present invention is based on the identification of the main absorbance peaks in the test sample, and for that reason this is also referred to as method of the main peaks.

In at least one embodiment, the method of comparing spectra originally proposed in the present invention will be described for comparing spectra of drugs or pharmaceutical ingredients, presented in tablets, powders or liquids.

Thus, by comparing the sample spectrum with the spectra of the reference library, it will be possible to identify, for example, which sample (product) is under review.

Anyway, it is emphasized that such embodiment should be construed only as an exemplary embodiment of the invention, not resulting in a limitation thereof. In alternative embodiments, the same method of comparing spectra proposed in the present invention could be used to compare spectra of other materials unrelated to drugs or pharmaceutical ingredients.

Figure 1:
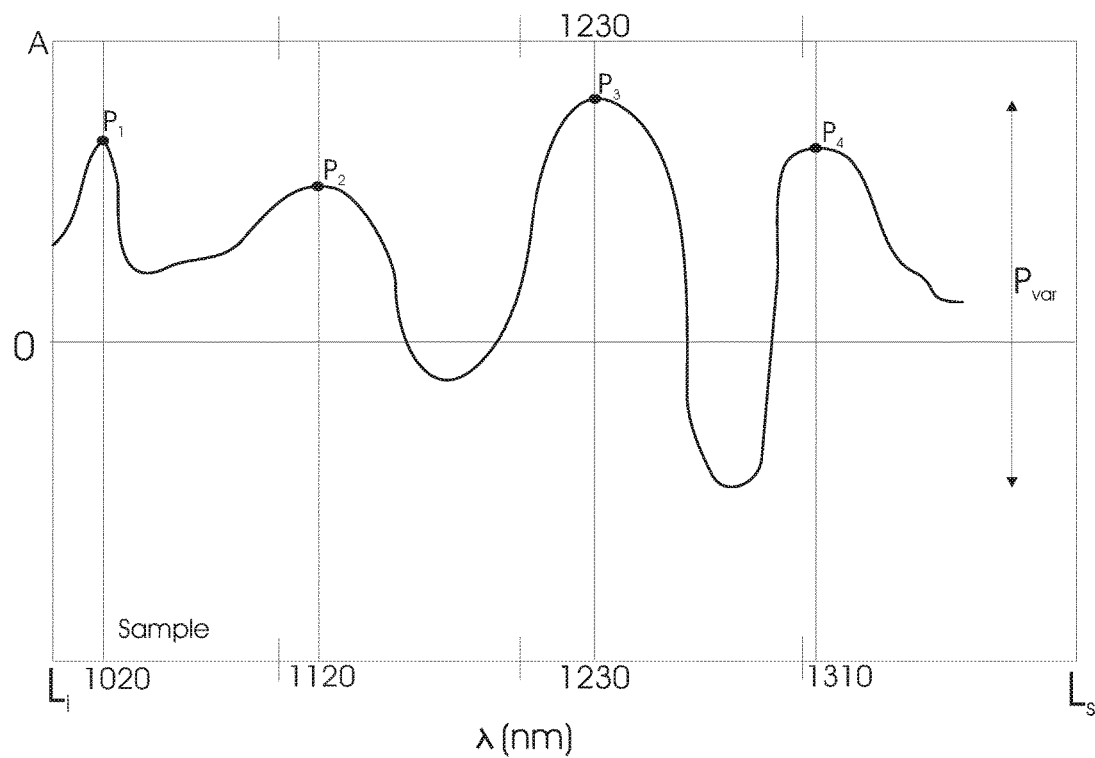
FIG. 1—is the representation of a test sample spectrum, highlighting the relevant spectral peaks of the sample.

In an initial step, and referring to FIG. 1, the method for comparison of spectra proposed in the present invention, called Major Peaks Method comprises the step of obtaining at least one relevant spectral peak P1, P2, P3 and P4 . . . Pn from a sample spectrum.

By main spectral peaks P1, P2, P3, P4 . . . Pn of the sample spectrum, it is understood the most relevant peaks of the sample, or in other words, the peaks with maximum heights absorbance in the sample spectrum. In at least one embodiment, the spectral peaks considered relevant can be obtained from the first derivative of the sample spectrum.

For the automatic determination of relevant P1, P2, P3 and P4 sample spectral peaks, it is determined if a given sample absorbance peak value is above a predetermined limit. In at least this exemplary embodiment of the present invention, the spectral peaks P1, P2, P3 and P4 were considered relevant when they presented height (value) greater than or equal to 5% of a variation parameter Pvar.

Obviously, it is understood that the 5% limit in relation to the variation parameter Pvar can be defined by the user of the method for comparison of spectra proposed in the present invention.

In certain desirable embodiments, said variation parameter Pvar is calculated as the maximum amplitude of the spectrum, that is, the difference between a maximum absorbance value and a minimum absorbance value in the sample spectrum.

In addition, for an optimization of the method for comparison of spectra proposed in the present invention, a sample spectrum region of interest should be defined to determine the relevant spectral peaks P1, P2, P3 and P4.

After the definition of said region of interest, it is possible to avoid evaluation of the whole sample spectrum, thus saving hardware and software resources, and time for the comparison of the spectra.

In at least this embodiment of the proposed method, and with reference to FIG. 1, the region of interest is defined respectively by its lower and upper limits Li and Ls, limits that are equivalent to existing wavelength values within the region related to near infrared spectroscopy (NIR).

Thus, it is understood that the region of interest illustrated in FIG. 1 comprises spectra between 1000 nm (Li) to 1400 nm (Ls). Even more desirably, the user of the method of comparison between of spectra proposed in the present invention has the freedom to constrain the values of the region of interest depending on the properties of the sample to be compared. That is, although it is possible to obtain a spectrum in almost the entire length of NIR, it is only possible to define the region of interest where the library materials are more responsive, thereby reducing processing time and resources.

As shown in FIG. 1, in at least this exemplary embodiment of the method of comparison of spectra proposed in the present invention, the relevant spectral peaks P1, P2, P3 and P4 were respectively identified in the following wavelengths: 1020 nm, 1120 nm, 1230 nm and 1310 nm.

After defining the spectral peaks considered relevant P1, P2, P3 and P4 of the sample in the respective wavelengths, one should compare each relevant spectral peak P1, P2, P3 and P4 with the spectra of the reference library Pref1, Pref2, Pref3.

As discussed previously, the reference library stores at least one spectrum of a known substance, wherein said spectrum of the known substance includes a spectral peak, that is, the peak with the highest value.

Figure 2:
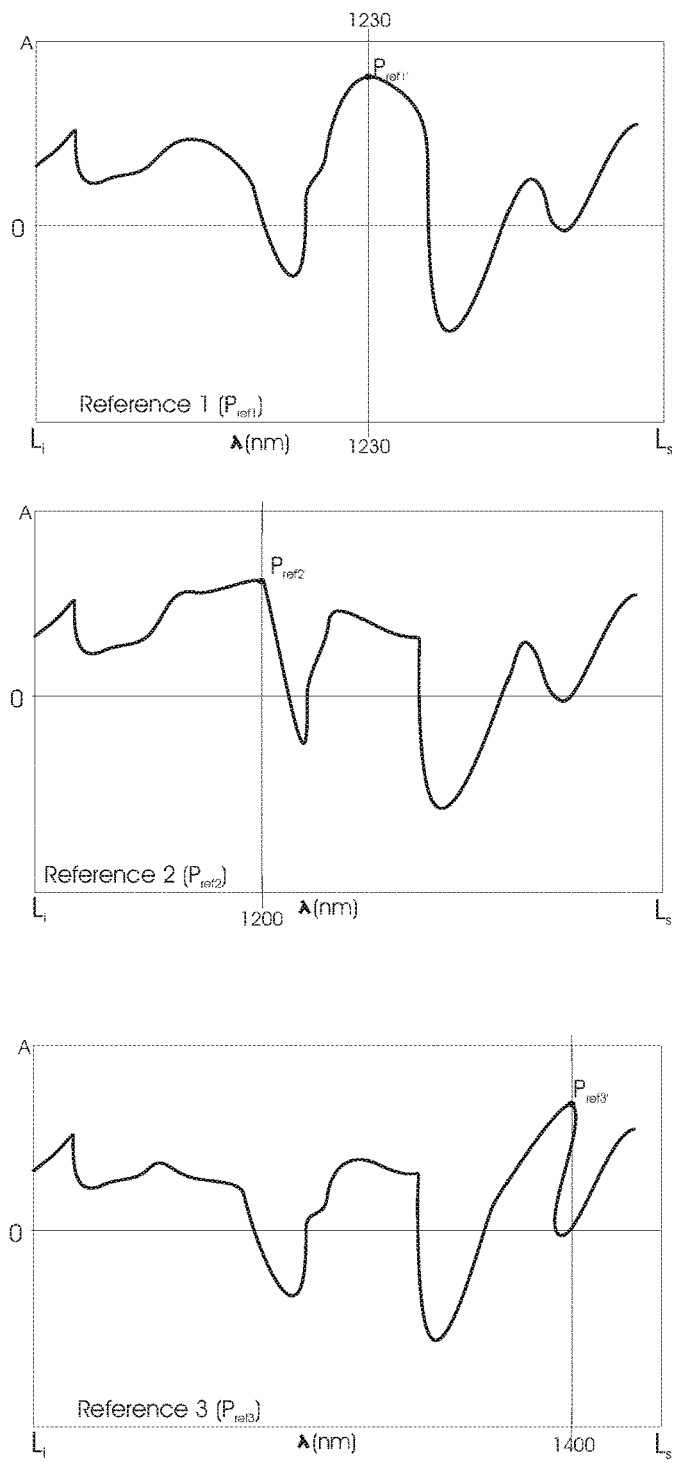
FIG. 2—is a schematic representation of the spectra of three hypothetical reference materials contained in a reference library.

Thus, it is understood that each of the spectra of the reference library Pref1, Pref2, Pref3, comprises a particular spectral peak. FIG. 2 illustrates an optimal representation in which the reference library comprises the spectrum of three known components Pref1, Pref2, Pref3, each respectively comprising a reference spectral peak Pref1', Pref2', Pref3'.

More specifically, the method of comparison of spectra proposed in the present invention compares each relevant spectral peak of the sample P1, P2, P3 and P4 with reference spectral peaks Pref1', Pref2', Pref3'.

Thus, it is understood that the relevant sample peaks P1, P2, P3 and P4 are compared with reference spectral peaks Pref1', Pref2', Pref3' of the components in the reference library.

Figure 3:
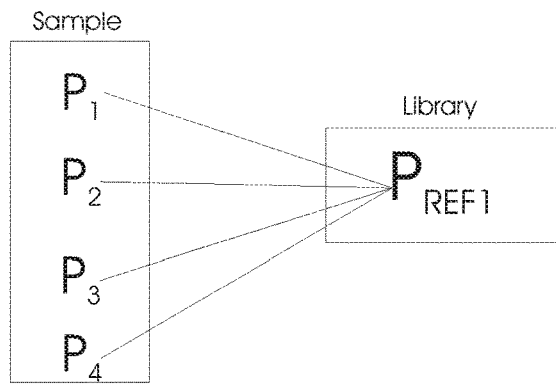
FIG. 3—is a representation of the embodiment of the equivalence comparison and analysis stage between the sample's relevant spectral peaks with the spectra of a reference library.
Figure 3:
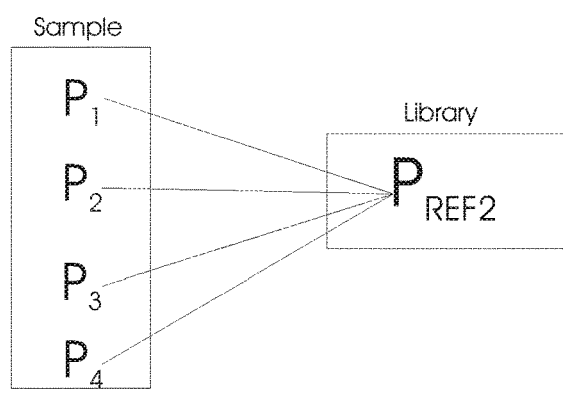
Figure 3:
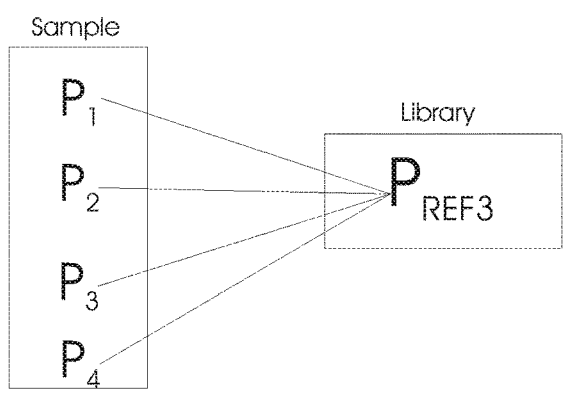

With reference to FIGS. 1 to 3, initially the relevant spectral peaks of the sample P1, P2, P3 and P4 are compared with the first reference spectrum Pref1. More specifically, this comparison will verify whether there is an equivalence of one of the relevant sample peaks P1, P2, P3 and P4 with reference spectral peak Pref1 in the first reference.

In other words, there should be a verification of whether the wavelength of one of the relevant sample peaks P1, P2, P3 and P4 is equivalent to the reference spectral peak Pref1'.

In this case, and with reference to FIGS. 1 to 3, there is an equivalence between the relevant spectral peak P3 of the sample (third relevant spectral peak) with reference spectral peak Pref1', since both the third relevant spectral peak P3 and reference spectral peak Pref1' were obtained at 1230 nm. Thus, the component with the reference spectrum 1 should be considered as a potential candidate to represent the test sample.

Subsequently, the same step is performed for the comparison and analysis of equivalence between the spectrum of references 2 and 3 and the relevant spectral peaks P1, P2, P3 and P4 of the sample as shown in FIG. 3.

In at least this desirable embodiment of the method of comparison between spectra illustrated in FIGS. 1 to 3, the only equivalence identified between sample and reference occurred between the reference substance 1 and the third relevant spectral peak P3 of the sample (third relevant spectral peak), since none of the other relevant spectral peaks P1, P2 and P4 were detected at wavelengths of 1200 nm (reference 2) and 1400 nm (reference 3).

It is noteworthy that it is not necessary that the equivalence between the reference spectrum and the relevant peaks P1, P2, P3 and P4 of the sample occur for the relevant peak in the sample with greater height (highest value). In other words, the main reference peak should not necessarily be the highest peak of the sample, since the sample may comprise of a mix of several compounds.

However, the reference spectral peaks Pref1', Pref2', Pref3' should be equivalent (at the same wavelength) to one of the peaks considered relevant P1, P2, P3 and P4 in the sample.

Thus, it is understood that there may be equivalence between a given sample and more than one substance in the reference library, if that occurs, these substances should be identified as potential candidates to represent the test sample and the next steps should be performed in the proposed method, as further described below.

It is also understood as feasible to verify the equivalence between the relevant peaks P1, P2, P3 and P4 of the sample with the reference spectral peaks (Pref1', Pref2', Pref3') whose wavelengths do not coincide accurately, that is, it is acceptable to apply a definable tolerance for this match, so it is considered that there may be an offset between one of the relevant peaks P1, P2, P3 and P4 of the sample with the reference spectral peak Pref1', Pref2', Pref3' considered in a way as to ensure a tolerance, which is necessary due to the use of separate equipment for measuring samples where those reference spectra were constructed, as well as distortions related to the time of usage of each equipment.

In at least this desirable embodiment, a matching tolerance of 5 nm, for more or for less, is acceptable. Obviously, such a value can be adjusted according to the characteristics of the sample considered.

Furthermore, it is not necessary that the absorbance value between the sample peaks and the reference in which the equivalence is detected be equal, since the absolute values may vary among devices, usage time, etc., or in relation to FIGS. 1 and 2, it is not assumed that the relevant third spectral peak sample P3 should have the same absorbance value of the reference spectral peak Pref1', however, it is understood that these peaks must be detected at the same wavelength, taking into account the defined tolerance.

Having detected the equivalence between the sample spectrum and at least one spectrum of the reference library, the method of comparison of spectra proposed in the present invention is configured to analyze the shape of such spectra around the wavelength at which the equivalence was detected.

Thus, considering at least this desirable embodiment of the proposed method, one should correlate the relevant spectral peak P3 of the sample (third spectral peak material) with the reference peak spectral Pref1' around the wavelength of 1230 nm.

Figure 4:
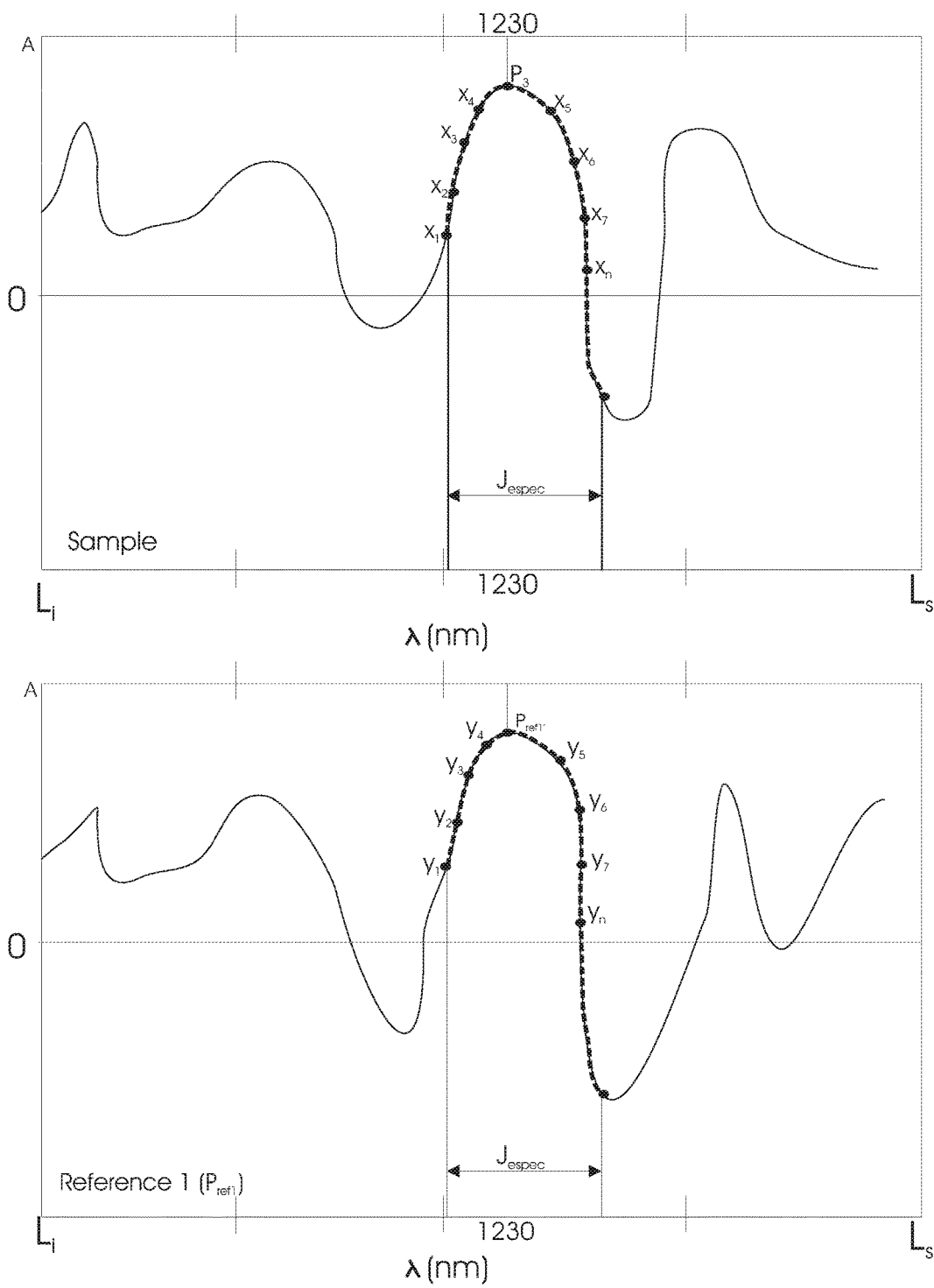
FIG. 4—is a graphical representation of the correlation of the sample's relevant spectral peak with the reference spectral peak.

In reference to FIG. 4, said correlation is performed on a Jespec spectral window defined around the coinciding wavelength between them.

The width of the Jespec spectral window around the wavelength at which the equivalence is detected is definable, so that in at least this embodiment a value of 25 nm to right and left was used, totaling an overall width of 50 nm. Thus, this embodiment of the spectral window Jespec considered values between 1205 nm and 1255 nm.

Thus, and referring to FIG. 4, one should correlate the absorbance value of each of the spectral points in the sample around the relevant spectral peak considered (third relevant peak P3) with the absorbance values around the reference spectral peak Pref1'.

In at least this embodiment and as represented in FIG. 4, the correlation is performed from the points x1, x2, x3 . . . xn around the relevant third peak P3 and the points y1, y2, y3 . . . yn around the 'reference spectral peak Pref1'.

The number of points around the equivalence wavelength used in the correlation may be preset by the user, and the illustration in FIG. 4 should not be considered a limitation of the present invention.

Desirably, the correlation between the spectra of the sample and the reference is performed using the Pearson correlation formula (product-moment correlation coefficient), as shown below:

$$\rho = \frac{\sum_{i=1}^{n}(x_i - \bar{x})(y_i - \bar{y})}{\sqrt{\sum_{i=1}^{n}(x_i - \bar{x})^2}\sqrt{\sum_{i=1}^{n}(y_i - \bar{y})^2}}$$

Where $x_i$ and $y_i$ represent respectively the absorbance of the sample and of the reference for the points in the Jespec spectral window with the same wavelengths as shown in FIG. 4, and $\bar{x}$ and $\bar{y}$ represent the average absorbance established within the spectral window Jespec for the sample and reference respectively.

It is noteworthy that the use of the Pearson correlation formula in the correlation step should be considered only as an exemplary and desirable description of the present invention, and is advantageous for being non-dependent on the vertical scales of the compared spectra.

Anyway, in alternative embodiments, other methodologies, such as the cosine similarity or Spearman correlation coefficient could be used.

Still desirably, after the correlation step is completed, the results obtained can be subjected to a hypothesis test to determine the statistical significance of the correlation. In at least one optimal embodiment, the t-student hypothesis test is used.

In addition to the method of comparing spectra described above that is based on matching the main sample spectrum absorption peaks and reference peaks (main peaks method), the present invention is also directed to a method of comparison of spectra which focuses on the analysis of the second derivative of the sample spectrum and the second derivative of the reference substance spectrum. This method is particularly relevant in cases where a main peak cannot be identified according to the criteria established above.

This proposed embodiment, also referred to as Variances Method, aims to capture more subtle features of absorption between the spectra, features which do not correspond to a significant absorbance peak as described above (Main Peaks Method).

These subtle absorption features have their effect amplified when one calculates (observes) the second derivative of the sample spectrum and the reference, to form regions of high variance.

Thus, this configuration of the spectra comparison method proposed in the present invention, referred to as Variances Method, should obtain a second derivative of the sample spectrum and the reference library spectrum.

In addition, to evaluate regions of more subtle absorption, one should determine a dispersion region Rdisp of the second derivative in the spectral reference library.

The dispersion region Rdisp is determined by calculating the variance of the second derivative values for each wavelength within the reference spectrum, or within the region of interest defined by its lower and upper limits (Li and Ls).

Figure 5:
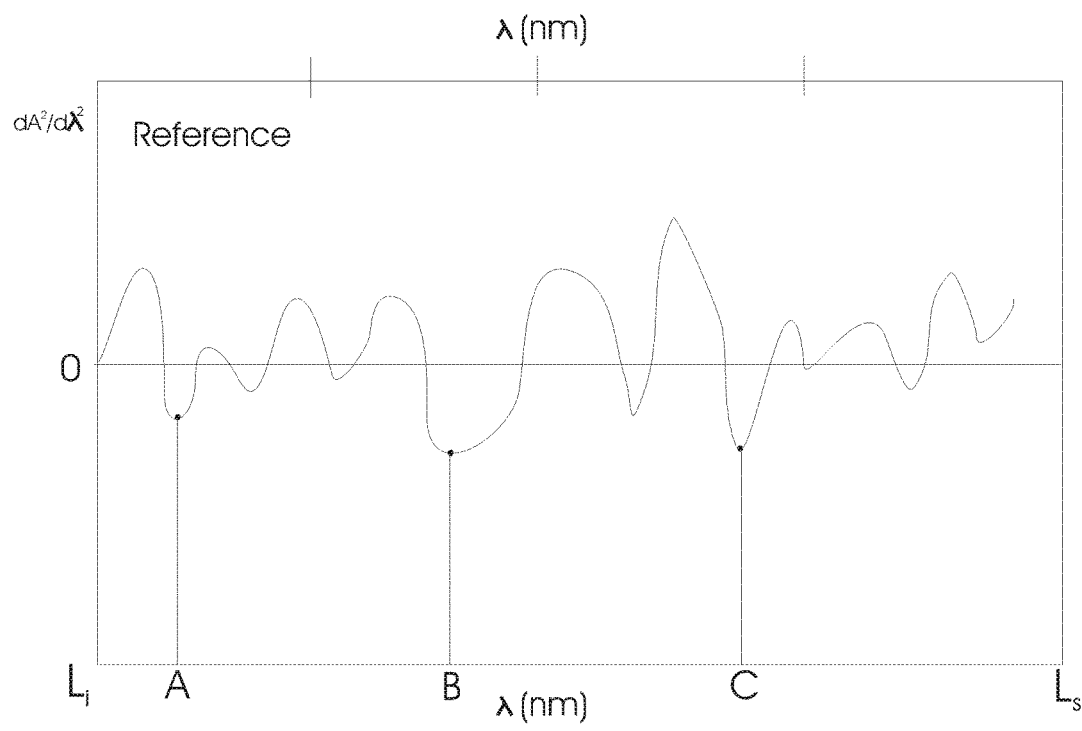
FIG. 5—is a representation of the second derivative of the reference library spectrum (reference spectrum)

FIG. 5 is a desirable representation of the second derivative of the spectrum reference library, defined by the region of interest between limits Li and Ls. To determine the Rdisp dispersion region, one should calculate the standard deviation of the second derivative of the absorbance for each point (each wavelength) on the region of interest in a region of 20 nm above and below each point.

The value of 20 nm, referred to as dispersion range may of course be adjusted depending on the properties of the sample into consideration.

Thus, it is understood that the dispersion region Rdisp is obtained from the calculation of at least one dispersion parameter related to the wavelengths of the spectrum in the reference library, and more specifically its second derivative.

Thus, referring to the wavelength shown by point A in FIG. 5, we calculate the standard deviation of the values of the second derivative of absorbance at wavelengths in the region of 20 nm above and below point A.

The same methodology is performed for the next wavelength in the region of interest, in this case, as shown in the illustration in FIG. 5, the wavelength represented by points B and C. Thus, the standard deviation in the second derivative of the absorbance values in wavelengths in the region of 20 nm above and below points B and C, respectively, is calculated.

Thus, it is understood that the same wavelength can be counted in more than one standard deviation calculation, additionally, the representation of wavelengths referenced in points A, B and C in FIG. 5, must be seen only as an exemplary representation of the present invention.

Given the standard deviation for each point within the region of interest, the Rdisp dispersion region is, in at least one embodiment, defined by points with a standard deviation between the 50% points with higher standard deviation (equal to or higher than the median standard deviation).

Figure 6:
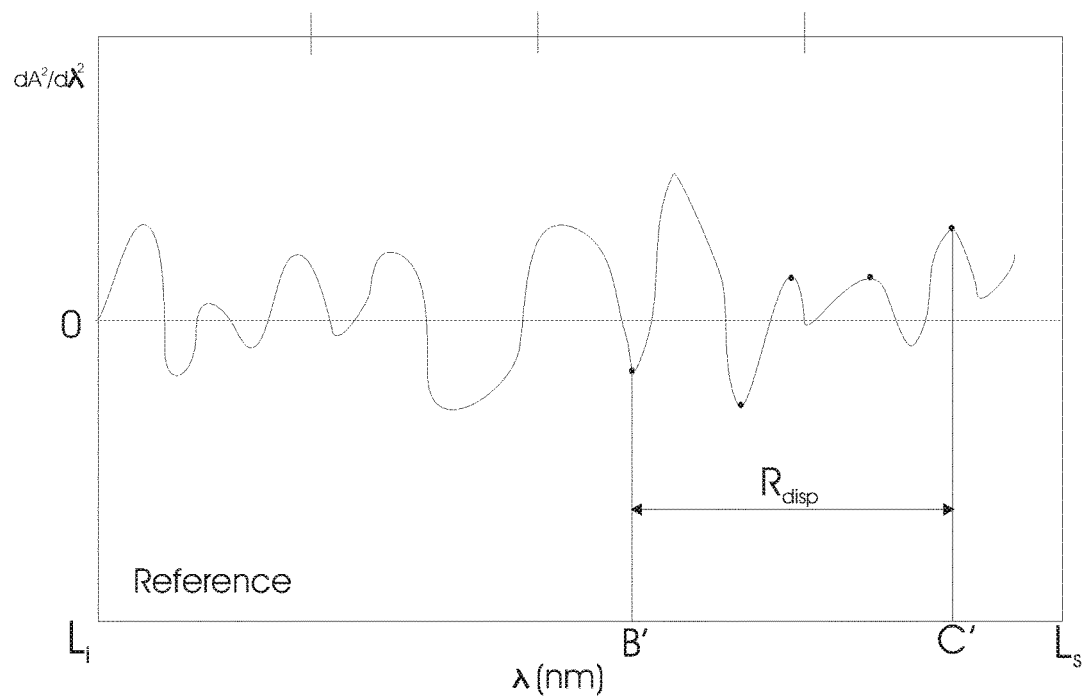
FIG. 6—is a schematic representation of the dispersion region of the second derivative of the reference library spectrum.

FIG. 6 illustrates an exemplary representation of the Rdisp, dispersion region, in this case limited by wavelengths represented by points B' and C'.

After obtaining the dispersion region Rdisp in the reference library spectra, the limits of said region, that is, wavelengths B' and C', should also be considered as the limits of the Rdisp dispersion region of the sample spectrum. In other words, even though it was obtained from the second derivative of the reference library spectrum, the Rdisp dispersion region is transported to the sample spectrum, and more specifically to the second derivative of the sample spectrum.

Figure 7:
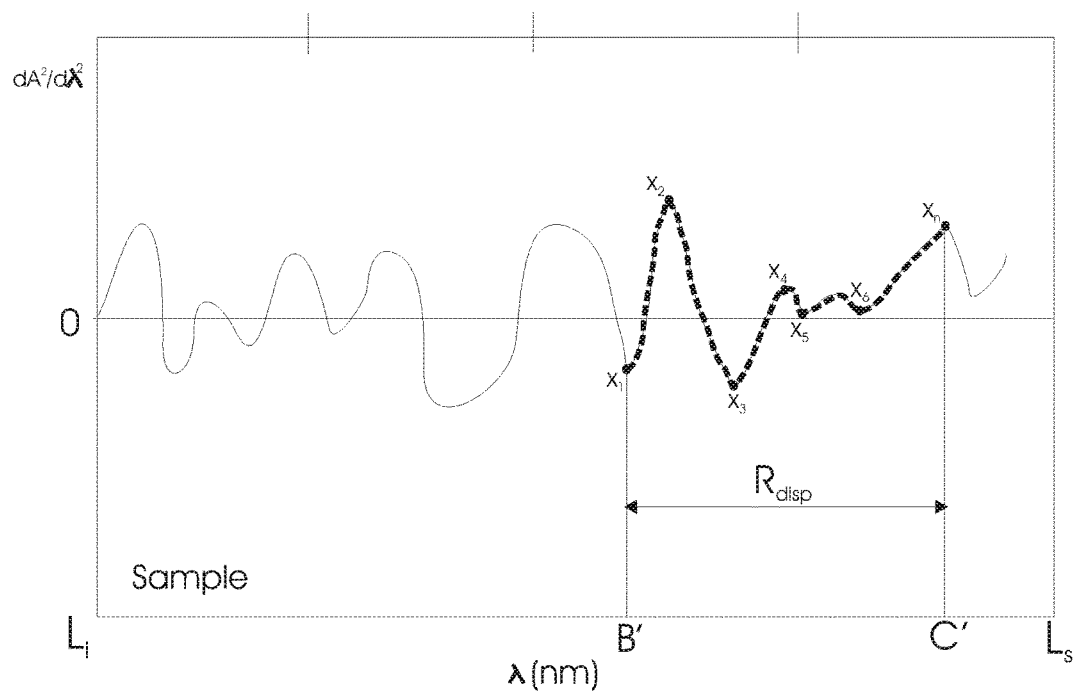
FIG. 7—is a representation of the correlation of the second derivatives of the sample spectrum and the reference spectrum.
Figure 7:
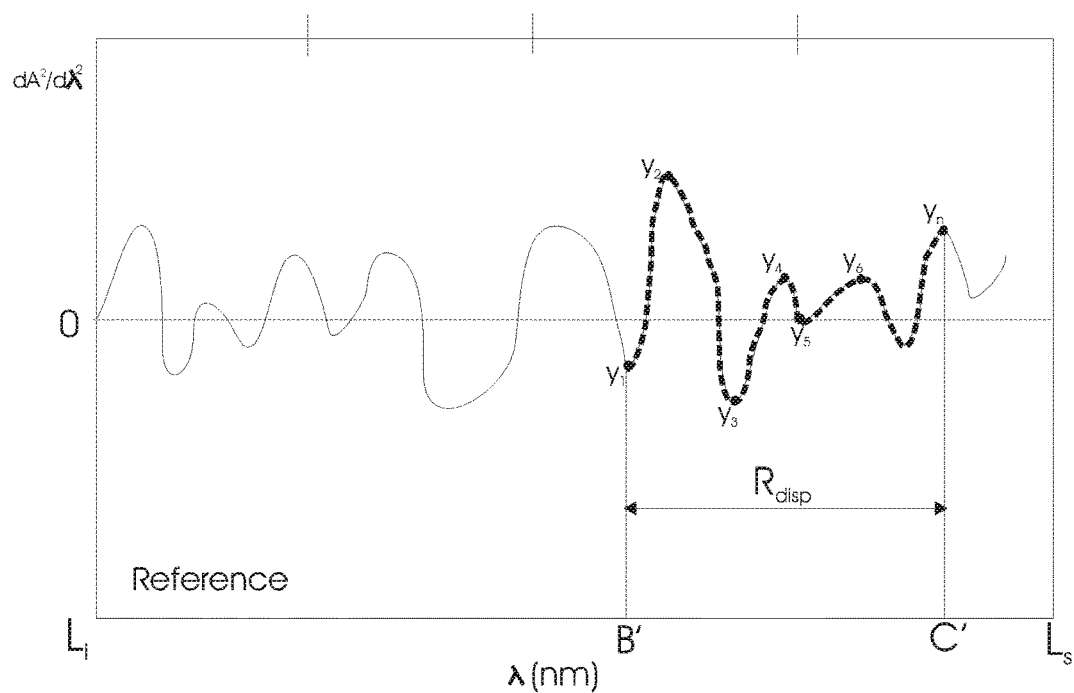

Thus the limits of both the sample and reference are defined to perform the correlation between the values of the second derivative of the absorbance in the sample (x1, x2, x3, x4, x5, x6 ... xn) and of the second derivative of absorbance in the reference library spectra (y1, y2, y3, y4, y5, y6 ... yn), as shown in FIG. 7.

As in the description referring to the Main Peaks Method, the Variances method correlates spectra, for example, using the Pearson correlation formula below:

$$\rho = \frac{\sum_{i=1}^{n}(x_i - \bar{x})(y_i - \bar{y})}{\sqrt{\sum_{i=1}^{n}(x_i - \bar{x})^2}\sqrt{\sum_{i=1}^{n}(y_i - \bar{y})^2}}$$

However, and as previously mentioned, in the Variances Method, the correlation is performed upon the second derivative of both the sample spectrum and the reference library spectrum. Thus, xi (x1, x2, x3, x4, x5, x6 ... xn) and yi (y1, y2, y3, y4, y5, y6 ... yn) respectively represent the values of the second derivative of the absorbance of the sample spectrum and the second derivative of the reference library spectrum within the Rdisp, dispersion region, as represented in FIG. 7.

Obviously, using the Pearson correlation formula for the correlation between the second derivatives must be considered as an exemplary description of the Variances Method, alternatively other means of obtaining the correlation statistics could be used.

Having correlated the second derivatives, the results obtained should be subjected to a hypothesis test to determine the statistical significance of the correlation. In at least one optimal embodiment, the Student's t hypothesis test should be used.

As described above, the present invention proposes a method of comparison of spectra based on the behavior of the second derivative of spectra both in a sample and in a reference library, which is especially useful when the first method, the Main Peaks Method cannot be implemented.

In this way, one can evaluate more specific spectra behaviors (subtle, faint), allowing to check whether the spectrum of the test sample is equivalent to a spectrum of a reference library and therefore, if the test sample corresponds to the substance whose spectrum is stored in the reference library.

Additionally, it is important to emphasize that the method of spectral comparison entitled Variances Method can be used independently for comparing spectra and can represent a more specific step (breakdown) of the method of comparison of spectra proposed in the present invention and entitled the Main Peaks Method.

Thus, and with reference to FIGS. 1 to 4 and their respective descriptions, if the equivalence of the relevant spectral peaks P1, P2, P3 and P4 and reference spectral peaks Pref1 Pref2', Pref3' is not detected, one can determine the second derivative of the sample spectrum and reference library spectra and then correlate them in the Rdisp. dispersion region.

Thus, even if no similarity is detected between the spectra when considering only their most relevant peaks, one can analyze the second derivative thereof in order to assess more subtle similarities between the spectra and consequently assess whether the test sample equals the substance whose spectrum is stored in the reference library.

Having compared the spectra in the sample and in the reference library, either through the methodology referred to as Main Peaks Method, Variances Method or a combination thereof, the obtained results should be disclosed.

In at least one exemplary embodiment, it is proposed that the final result of the comparison is displayed in a list of components whose spectra are saved in the reference library, listed in descending order of similarity (correlation values) with the sample spectrum.

In certain embodiments, initially one should list the components whose equivalence between one of the relevant spectral peaks P1, P2, P3 and P4 in the sample has been detected with the reference spectral peaks Pref1', Pref2', Pref3' 'in the reference library. For a better user view, such list may be made in descending order of the calculated Pearson correlation coefficient.

Next one lists the components whose reference spectral peaks Pref1', Pref2', Pref3' are not present in the sample spectrum, in descending order of the correlation coefficient between the second derivatives of the spectra.

It is also possible to list the reference library components obtained exclusively from the correlation between the second derivatives of the sample spectra and the reference library.

Obviously, the way the obtained results are displayed does not represent an exemplary and optimal embodiment of the present invention and the present description should be considered only as an exemplary description.

In addition to the method of comparing spectra described in the present invention and referred to as Main Peaks Method and Variances Method, it is also described a method of spectral comparison with prior identification of the major component of a sample, the Triangulation Method.

In this case, it is known that the component to be identified is present in minor proportion in the sample and the major component is previously known.

In Practical applications, it is frequently necessary to identify a secondary component, where a major component is previously known to exist in the formula, and whose spectrum is going to dominate the formula's spectrum. In the field of medicines for instance, the major component of a medication is usually identified from the information provided in the consumer or professional leaflets, label of the product, or publicly available safety datasheets.

Thus, the user of the proposed method must previously identify (indicate) which is the major component present in the sample and compare it with the sample and the information in the reference library.

It is noteworthy that in this case, the relevant component to be identified is a secondary component present in a smaller amount in the sample. The challenge is to identify this secondary component by comparison with the reference library. However, the sample should be regarded as a combination of the secondary and the major component which in turn has more influence on the spectrum of the sample. The secondary component is the component of interest, and is also further described as minor or reference component in the present method.

Thus, in the related scope of pharmaceutical products, the secondary component can be exemplified as the active ingredient of the drug in situations where the dosage is very low and the major component refers to the main excipient of the medication. The sample's spectrum refers to the active principle and the excipient together.

Thus, the method of comparing the spectra with the prior identification of the major component proposed in the present invention, comprises the steps of obtaining a spectrum of a sample and a reference, and identifying in advance the major component present in the sample.

Subsequently, one must correlate not only the sample spectrum with the reference spectrum, but also the reference spectrum with the spectrum of the major component. It is noteworthy that the major component of the spectrum must be previously known.

Figure 8:
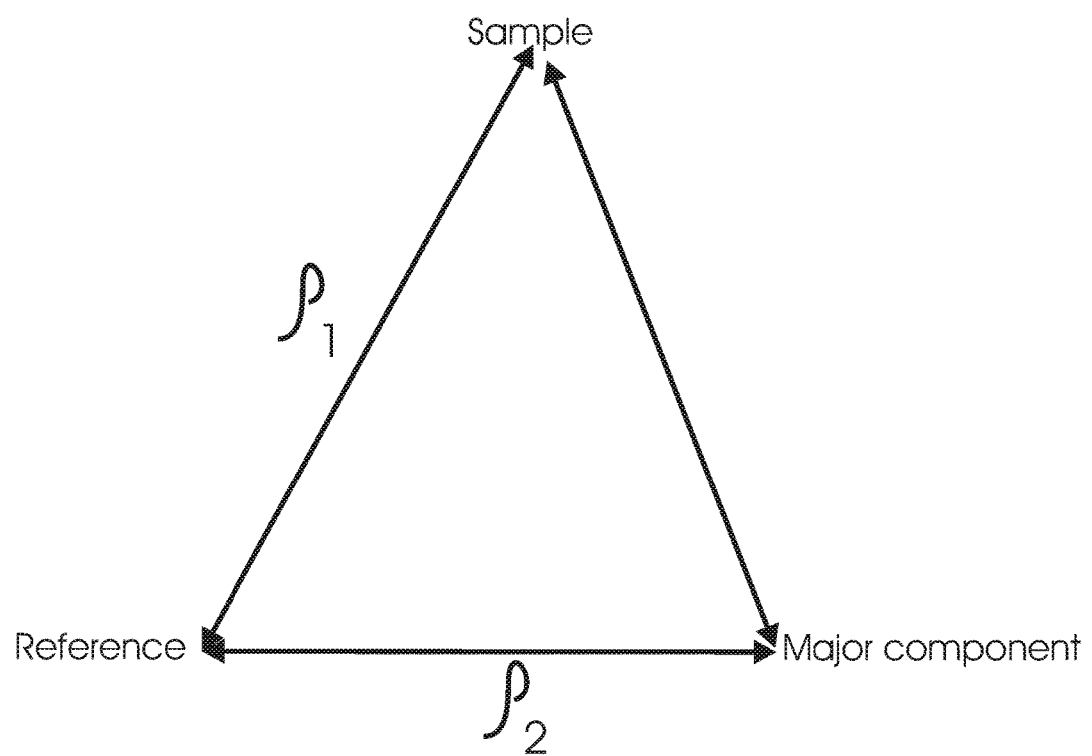
FIG. 8—is a representation of the triangular correlation step proposed in the present invention.

Therefore, and as illustrated in FIG. 8, a triangular correlation is carried out, where the "corners" of said triangle are respectively equivalent to the sample, to the reference and to the major component. It is expected that the correlation between the major component and the sample is greater than the correlation between the sample and the reference (secondary component). However, a better correlation is also expected between the sample and the secondary component than the correlation between the major and secondary components. The proposed analysis is based on this difference. The larger it is, the more significant the signature of the secondary minor component in the sample spectrum will be.

In certain embodiments, the triangular correlation is performed within the range (wavelengths) defined by a dispersion region Rdisp. As already described with reference to the Variances Method, the Rdisp dispersion region is obtained from the second derivative of the reference spectrum.

Figure 9:
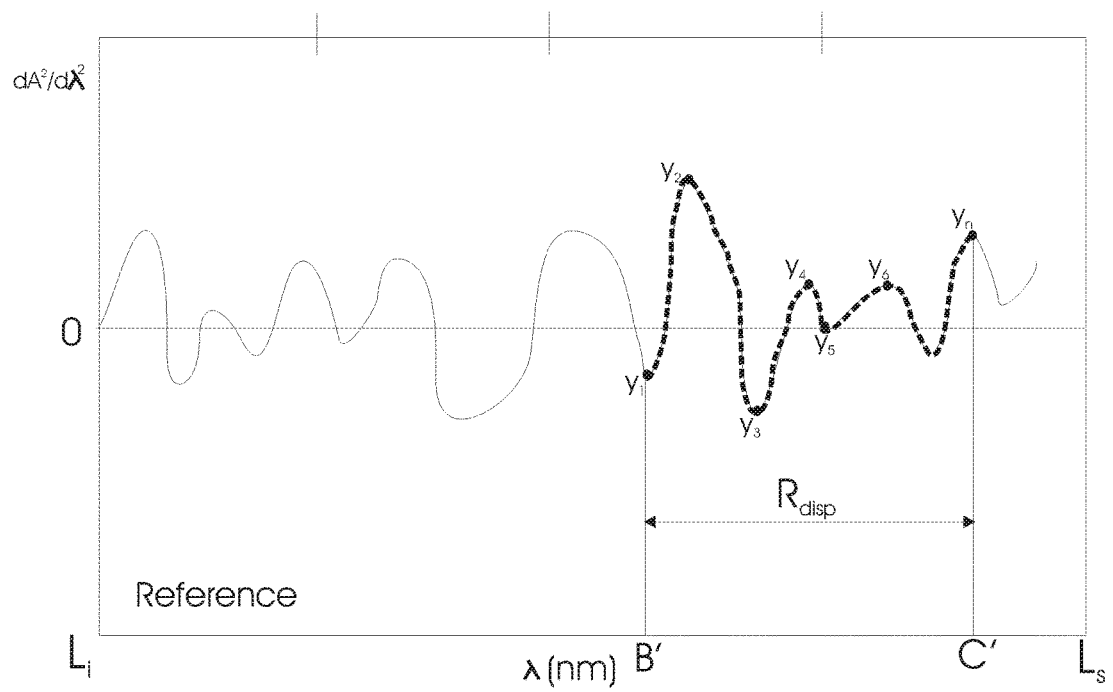
FIG. 9—is a representation of the dispersion region obtained from the second derivative of the reference spectrum.

As can be seen in FIG. 9, at least this embodiment of the method of comparison between spectra with identification of the major component of a sample, dispersion region Rdisp is defined by the wavelength equivalent to points B' and C'.

Also and as already described with reference to the Variances Method, the dispersion region is defined through the calculation of the variance of the values of the second derivative of absorbance for each wavelength in the reference spectrum, and within the region of interest defined by its lower and upper limits (Li and Ls).

Thus, to determine the Rdisp dispersion region, one should aim to calculate the standard deviation of the values of the second derivative of absorbance at each point (each wavelength) in the region of interest in a region of 20 nm above and below each wavelength.

Therefore, it is understood that the Rdisp dispersion region is obtained from the calculation of at least one dispersion parameter related to the wavelengths in the spectrum of the reference library, and more specifically its second derivative.

After determining the standard deviation for each point within the region of interest, the Rdisp dispersion region may be limited by points whose standard deviation is between the 50% points of greater standard deviation (with values equal to or greater than the median standard deviations), in this case, and as illustrated in FIG. 9, limited by wavelengths B' and C'.

It is important to note that the proposed methodology for calculating the Rdisp dispersion region in the method of comparison of the spectra with the identification of the major component, is the same which is performed in the description of the Variances Method.

Figure 10:
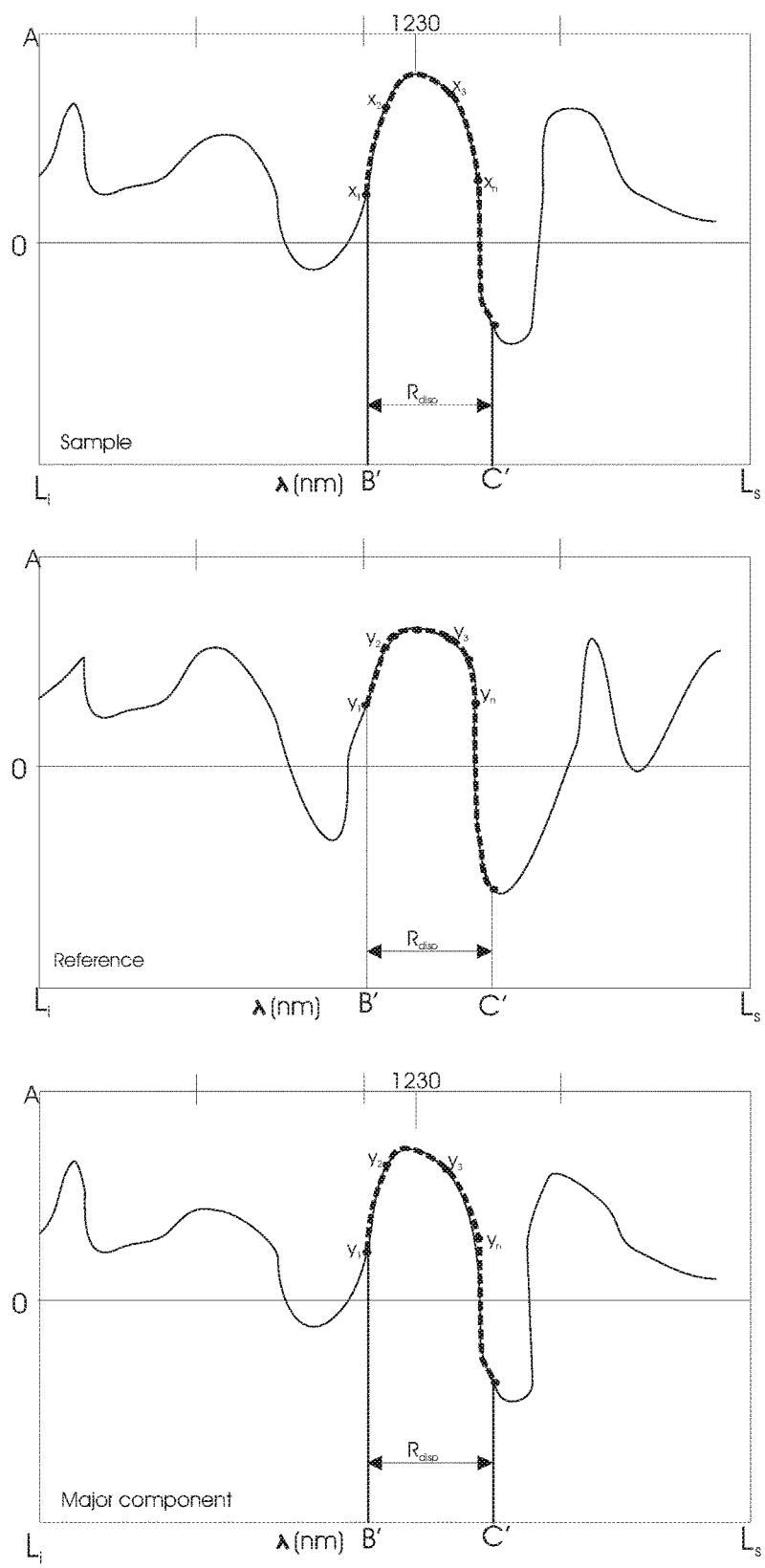
FIG. 10—is a representation of the limits of the dispersion region in the spectra of the sample, reference and major component.

After defining the Rdisp dispersion region in the second derivative of the reference spectrum, the limits (wavelengths) of such region are transported to the spectra of the sample, of the reference and of the major component, as shown in FIG. 10. Subsequently, the triangular correlation between these spectra is performed, for example, from the Pearson Correlation formula, already mentioned above.

Therefore, one correlates the spectrum of the major component and the sample, the major component and the reference, and the reference and the sample.

Since a larger proportion of the sample is formed by the major component and a reduced proportion by the reference component, it is expected that the correlation between the sample and the major component have a high value of the Pearson coefficient.

In addition, the correlation between the reference and the major component should have a lower value when compared to the value of the correlation between reference and sample, since the reference component is present (even in a smaller proportion) in the sample and is not present in the major component.

Figure 11:
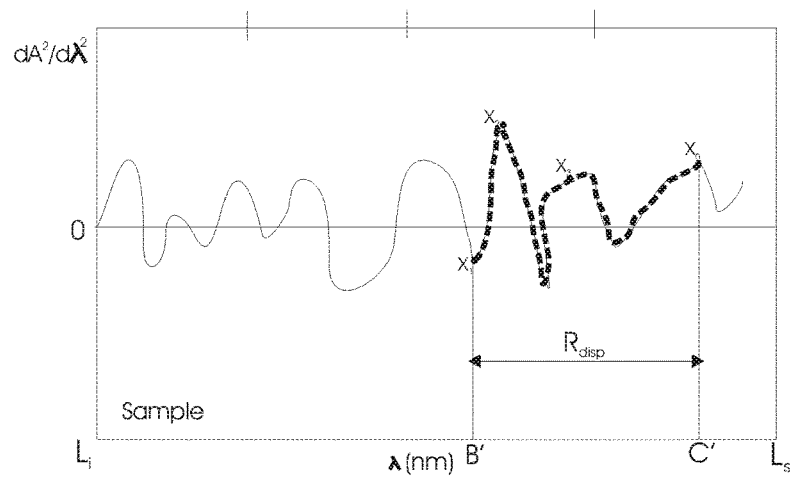
FIG. 11—is a representation of the correlation between the second derivatives of the sample spectra, reference and major component.
Figure 11:
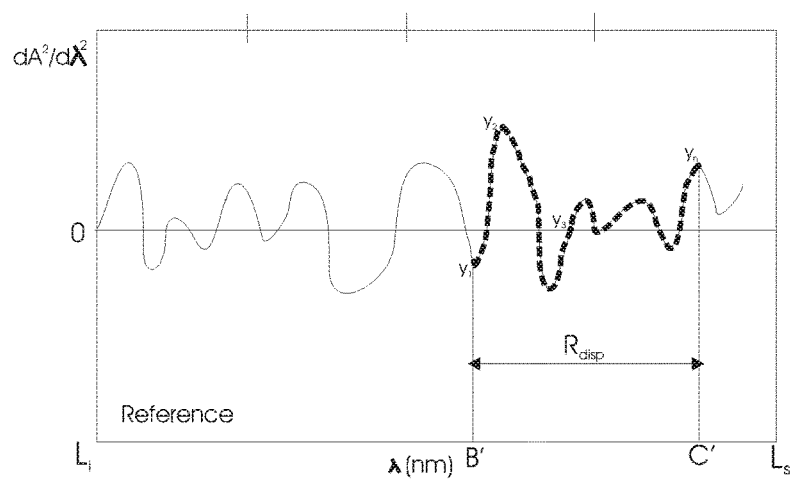
Figure 11:
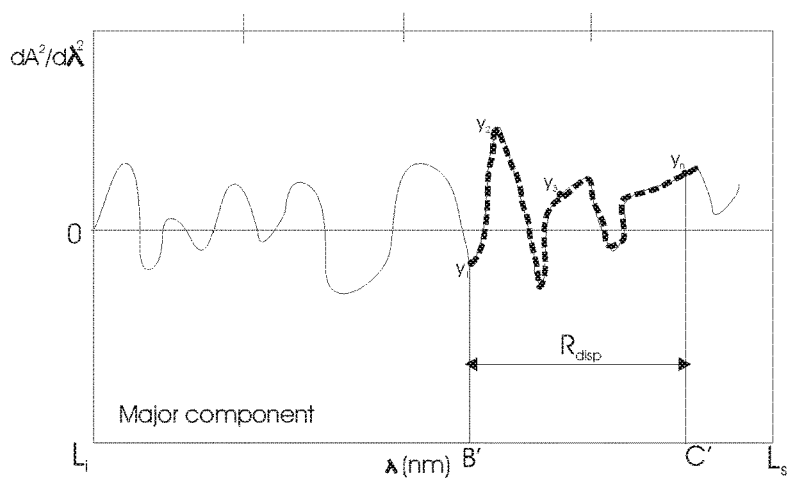

If the objective is to detect more specific behaviors of the spectra (sample, reference, and major component), it is possible to correlate the second derivative of those spectra, still considering the limits of the Rdisp dispersion region defined by the B' and C' wavelengths and as seen in FIG. 11.

Having obtained the value of the correlations, the method of comparison of the spectra with the identification of the major component of a sample, comprises the step of subtracting from the value obtained from the correlation between the reference spectrum with the spectrum of the sample the value obtained in the correlation between the reference spectrum and the spectrum of the major component.

In other words, as the representation in FIG. 8, attributing the $\rho 1$ reference to the correlation between the reference and sample and $\rho 2$ the correlation between reference and major component and assuming $\rho 1=0.3$ and $\rho 2=0.1$, the following should be determined:

$$D=\rho_1-\rho_2;$$

In certain embodiments, a hypothesis test, such as the Steiger's Z test, should be applied to the values to determine the significance of the values obtained. It is also proposed to apply Fischer's Z-transformation to the values of the correlations since these do not necessarily follow the normal probability distribution.

Obviously, the application of Steiger's Z test as a hypothesis test, should be considered only as an exemplary and optimal embodiment of the present invention.

Thus, with said step of subtracting between correlations (and not from the spectral curves), basically the effects of the major component in the calculations is neutralized and it becomes possible to evaluate whether the sample comprises a certain active ingredient whose spectrum is previously stored in a reference.

In at least one embodiment, the result obtained by subtracting the correlations revealed to the user of the Triangulation Method in descending order, i.e. the greater the difference between the correlations, the more likely the candidate will be a minor component.

It is important to note that in some cases the challenge is not necessarily the identification of unknown components present in the sample, but to ensure that items appearing in lists of restricted or prohibited goods are not present.

Thus, the reference substance libraries are not so large, having something around 20 to 30 elements, and the objective is only to identify the samples suspected of having some restricted or prohibited component.

An alternative use of the method proposed in the present invention is to test for the presence of a known component, for example, when one wishes to determine whether or not a certain medication contains a specific active ingredient present in the reference library.

This is very useful in identifying formulated products containing ingredients that are not allowed in small quantities, along with another major component. The spectral signature of the unauthorized component must be present in the spectrum of the sample of the medication, but because the component is present in small quantity, the sample spectrum would not produce a significant correlation with the reference spectrum of the minor component. Thus, the spectrum of the sample will be more associated with the reference of the major component, and it would be necessary to neutralize this effect through the proposed triangulation to identify formulations that may contain an unauthorized minor component.

In addition to the methods for comparison of spectra proposed in the present invention and referred to as Main Peaks Method, Variances Method and sample Triangulation Method, the present invention also covers a a portable device 1 suitable for carrying out the methodologies described above.

Figure 12:
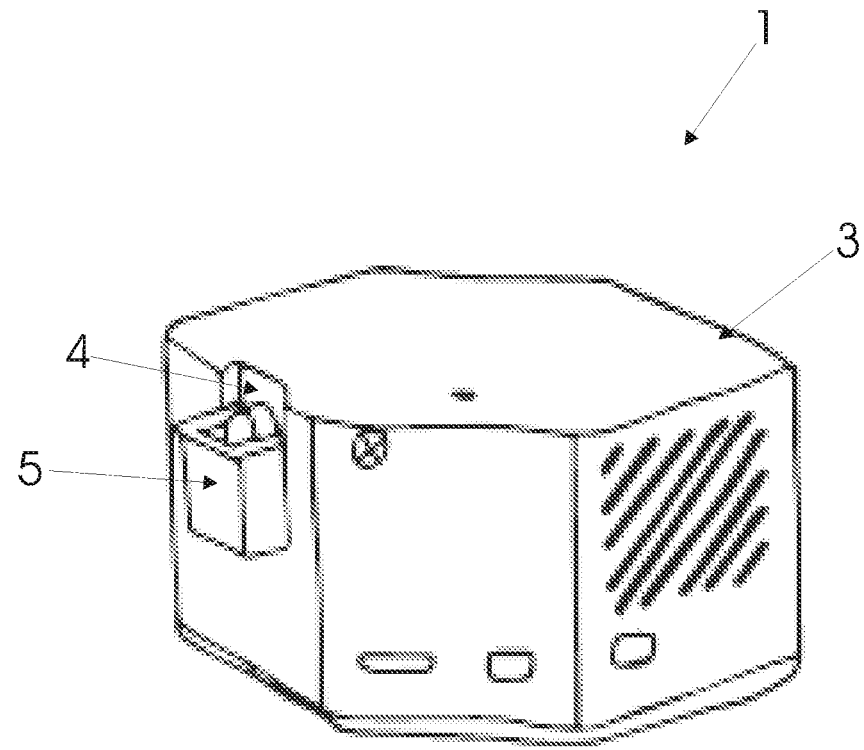
FIG. 12—is an exemplary representation of the portable device used to evaluate a sample spectrum as proposed in the present invention.

With reference to FIG. 12, the portable device 1 to evaluate the spectrum of a sample proposed in the present invention, also referred to as device 1, is basically provided with a housing 3 and a measuring window 4.

In certain examples of hexagonal shape, device 1 is provided with dimensions that allow transportation and handling without major drawbacks, capable of being easily used by one person.

Inside housing 3, device 1 comprises a spectral reading element (not shown), which can illuminate the sample with a source of electromagnetic waves and evaluate the radiation reflected by such a sample at various wavelengths.

In certain embodiments, the spectral reading element comprises two tungsten light bulbs, an optical assembly to collect and decompose the radiation reflected by the sample and a micro mirror matrix driven electronically which direct one wavelength at a time to a single InGaAs sensor (Indium, Gallium and Arsenic sensor).

Measuring window 4 should be understood as a slight opening in housing 3, able to receive the sample to be identified. In at least one embodiment, one should use one of measuring support 5 for the correct positioning of the sample.

Said support 5 should in certain embodiments be made of polymer material covered with opaque metal plates, and still in at least one embodiment, be painted with white paint with titanium dioxide based pigment. It is understood that depending on the sample to be analyzed (solid, liquid or powder), said support 5 may comprise a particular shape.

Some embodiments for the measuring support 5 are illustrated in FIG. 13, in which the configuration in FIG. 13 (*a*) is used as a bottle for storage of liquid or powder sample, and the configurations in FIGS. 13 (*b*) and 13 (*c*) constitute supports for solid samples.

The measuring support 5 associated with measuring window 4 occurs in certain embodiments by sliding support 5 on existing rails on the side of window 4. FIG. 12 shows device 1 in which support 5 shown in FIG. 13 (*b*) is combined with measuring window 4.

It is noteworthy that the use of rails on the sides of the measuring window is only an exemplary embodiment of the invention, alternative embodiments could use any fastening means that allows the sample to be disposed in all the measurements, always at the same distance and position in relation to the spectral reading element.

Calibrating device 6, as shown by way of example in FIG. 14, was developed to guarantee the same comparison basis of readings taken between different devices or in only one device over time and space, considering the need to adjust the calibration due to differences in temperature and humidity between the various readings.

When calibrating in a uniform, standardized way, it is possible to make a comparison of new samples and information on samples previously read and held in the reference libraries.

In certain embodiments, calibrating device 6 is configured as an opaque metal plate, painted in at least one embodiment with white titanium dioxide-based paint (such as measuring support 5), which fits (cooperating format) and runs perfectly on the rails located on both sides of measuring window 4, not allowing the input of external radiation, and maintaining a maximum distance of 0.5 mm from the said window 4.

When device 1 is not in use, calibrating device 6 also functions as a protective cover for measuring window 4. In FIG. 14 (*a*) calibrating device 6 can be observed during its positioning on window 4, whereas in the representation of FIG. 14 (*b*), calibrating device 6 is fully positioned.

For effective completion of the calibration of device 1, calibrating device 6 must be inserted, as represented in FIG. 14 (*b*), and then the spectral reading element must be triggered. Please note that for the calibration of device 1, no sample should be inserted into measuring window 4.

Thus, the present invention proposes a portable device for evaluating the spectrum of a sample whose dimensions allow its transportation and handling by one person, and can thus be easily used at checkpoints or anywhere the analysis of a sample is required.

Additionally, by arranging measuring window 4, measuring supports 5 and calibrating device 6, the same position is maintained for all measurements, ensuring that the sample is always arranged at the same distance from the spectral reading element.

Thus, the present invention also proposes a calibrating device 6 to be used with a portable device 1 for the evaluation of a sample spectrum.

Calibrating device 6, by way of example as illustrated in FIG. 14, can be combined with measuring window 4 in portable device 1, by using the fastening means arranged in measuring window 4, in which calibrating device 6 is configured as an opaque metal plate treated with titanium dioxide-based paint and in addition, calibrating device 6 is configured to establish a complete seal of measurement window 4. By complete sealing, it is understood that calibrating device 6 prevents the input of external radiation to the measuring window.

Regarding the method proposed in this invention, and different from techniques known in the art that compare samples using the entire spectrum, the present invention focuses on a few absorption features in the spectrum, increasing the speed in the process and allowing the comparison with thousands of substances in seconds.

Another advantage of the present invention is that it allows the identification of the components of a mixture, since the spectrum of this mixture will present influences of all relevant components and each component will leave their mark on the spectrum of the mixture at specific positions.

The proposed methodology, and referred to as the Main Peaks Method simulates the behavior of a human being when comparing the similarity between two spectra, pointing out the similarities and differences only in the regions limited by the most relevant absorption peaks, where all the correlation analyses are processed. The proposed methodology aims to provide machine analysis similar to that done by humans, but at high speed, accuracy and repeatability.

The method mentioned in this invention adopts the premise that in case the most relevant peak of the substance is not represented in the sample, the other peaks will hardly be. By restricting the analysis to the main peaks, it is possible to gain time.

In addition to the comparison from the main absorption peaks in the sample (Main Peaks Method), for the reference substances whose main absorption peak is not present in the sample spectrum, a comparison is made based on the second derivatives of the spectra, limited to the region of greatest variance of the second derivative of the reference spectrum (Variances Method).

This allows the search for more subtle features of absorption, not just representing a prominent peak of absorption. The calculation of the correlation between the second derivatives of the spectra provides a measure that allows ordering the reference substances in descending order of similarity to the sample.

Additionally, the present invention deals with a Triangulation Method, using the comparison of spectra with the previous identification of the major component of a sample, and performing a triangular relationship with the spectra of the sample, of the reference and the major component. This proposed methodology makes possible the identification of a component present in a minor amount in the sample.

Thus, the present invention represents a low cost and easy to operate alternative for comparing a sample spectrum to a reference spectrum, which also quite efficiently identifies the likely components in formulated products or pharmaceutical ingredients.

The development allows the reading of the sample spectrum and the comparison with a spectral reference library, consisting of thousands of elements within a few seconds. The spectral library may have various sources, and does not need to be built using the same equipment used to read the sample, which confers a high degree of scalability to the system. The use of the calibrating device and the sample fastening devices helps to standardize the readings.

The use of a low cost miniaturized portable device and cloud computing enables the widespread use of this technique by a large number of users in different geographical locations. The online comparison using digital libraries is not only fast, but also does not expire and allows the sharing of information among thousands of users in real time.

Finally, it is important to note that the approach of the concepts proposed in the present invention for the analysis and identification of pharmaceuticals should be considered only as an exemplary desirable feature of the present invention. It is understood that the proposed methods and devices can be used in comparing and analyzing spectra of different types of materials/components.

Having described an exemplary and desirable embodiment, it should be understood that the scope of the present invention comprises other possible variations, being limited solely by the wording of the appended claims, including therein the possible equivalents.

The invention claimed is:

1. Method of comparison of spectra from a sample spectrum and at least one spectrum of a reference library, the method comprising the steps of:
    obtaining at least one relevant spectral peak from the sample spectrum, and
    comparing each of the relevant spectral peaks with the spectra in the reference library,
    wherein:
        the relevant spectral peaks are identified from a sample spectrum variation parameter, and
        the relevant spectral peaks are obtained within a region of interest in the sample spectrum.

2. The method of comparison of spectra according to claim 1, wherein:
    each of the reference library spectra comprises at least one reference spectral peak, and
    the method further comprises the step of comparing each of the relevant spectral peaks of the sample with each of the reference spectral peaks of the reference spectra.

3. The method of comparison of spectra according to claim 2, further comprising the steps of:
    checking if there is an equivalence of one of the relevant spectral peaks of the sample with the reference spectral peaks of the reference spectra, and
    if an equivalence is detected, correlating the sample spectrum with the spectrum of the reference library around the relevant spectral peak of the sample and the reference spectral peak where the equivalence is detected.

4. The method of comparison of spectra according to claim 3, wherein:
    the step of correlating the sample spectrum with the spectrum of the reference library around the relevant spectral peak of the sample and reference spectral peak is performed within a spectral window, and
    the method further comprises the step of, within the spectral window, considering absorbance values of the sample spectrum and of the reference material spectrum during the correlation of the sample spectrum with the reference material's spectrum.

5. The method of comparison of spectra according to claim 3, wherein, if not detected an equivalence between one of the relevant spectral peaks of the sample and the spectral reference peaks of the reference spectra, the method further comprises the step of correlating a second derivative of the sample spectrum with a second derivative from the reference spectrum library in a dispersion region, the dispersion region obtained from the second derivative of the spectrum in the reference library.

6. A method of comparison of spectra according to claim 5, wherein the step of correlating the sample spectrum with the reference library spectrum and the step of correlating a second derivative of the sample spectrum with a second derivative of the reference library spectrum are performed through one of the following methods: Pearson correlation formula, cosine similarity and Spearman correlation coefficient.

7. A method of comparison of spectra from the spectrum of a sample and at least one spectrum of a reference library, the method comprising the steps of:
- obtaining a second derivative of the sample spectrum and of the spectrum in the reference library, and
- correlating the second derivative of the sample spectrum with the second derivative of the reference library spectrum,
- wherein the step of correlating the second derivative of the sample spectrum with the second derivative of the reference library spectrum is performed in a dispersion region, the dispersion region being obtained from the second derivative of the reference library spectrum.

8. The method of comparison of spectra according to claim 7, wherein the dispersion region is determined from calculating at least one dispersion parameter related to the wavelengths of the second derivative of the reference library spectrum, the dispersion parameter related to a dispersion range of the reference library spectrum.

9. The method of comparison of spectra according to claim 8, wherein, within the dispersion region, consider absorbance values of the second derivative of the sample spectrum and of the second derivative of the reference library spectrum during the correlation of the second derivative of the sample spectrum with the second derivative of the reference library spectrum.

10. A method of comparison of spectra with the identification of a major component of a sample, the method comprising the steps of:
- obtaining a spectrum of the sample and of a reference,
- previously identifying the major component present in the sample,
- correlating the sample spectrum with the reference spectrum, obtaining a first correlation value,
- correlating the reference spectrum with a spectrum of the major component, obtaining a second correlation value, and
- comparing the first correlation value with the second correlation value.

11. The method of comparison of spectra with the identification of the major component of a sample according to claim 10, wherein:
- the method further comprises the step of defining a dispersion region from a second derivative of the reference spectrum,
- the dispersion region is obtained from the calculation of at least one dispersion parameter related to the wavelengths of the second derivative of the reference spectrum, and
- the steps to correlate the sample spectrum with the reference spectrum and correlating the reference spectrum with the spectrum of the major component of the sample are carried out within the limits defined by the dispersion region.

12. The method of comparison of spectra with the identification of the major component of a sample according to claim 11, further comprising the step of subtracting from the value obtained for the correlation between the reference spectrum with the spectrum of the sample, the value obtained in the correlation between the reference spectrum with the spectrum of the major component.

13. The method of comparison of spectra with the identification of the major component of a sample according to claim 12, further comprising the steps of:
- correlating, within the limits defined by the dispersion region, the second derivative of the sample spectrum with the second derivative of the reference spectrum, and
- correlating, within the limits defined by the dispersion region, the second derivative of the reference spectrum with the second derivative of the major component spectrum.

14. The method of comparison between spectra with the identification of the major component of a sample according to claim 13, further comprising the step of subtracting from the value obtained for the correlation between the second derivative of the sample spectrum with the second derivative of the reference spectrum the value obtained from the correlation between the second derivative of the reference spectrum with the second derivative of the spectrum of the major component.

* * * * *